US011819562B2

(12) United States Patent
Ma et al.

(10) Patent No.: US 11,819,562 B2
(45) Date of Patent: Nov. 21, 2023

(54) COMPOSITION FOR DYEING KERATIN FIBRES AND USE THEREOF

(71) Applicant: L'OREAL, Paris (FR)

(72) Inventors: Jingmiao Ma, Shanghai (CN); Zhibing Liu, Shanghai (CN); Yuehuang Jiang, Shanghai (CN); Chi Yang, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/623,029

(22) PCT Filed: May 31, 2020

(86) PCT No.: PCT/CN2020/093636
§ 371 (c)(1),
(2) Date: Dec. 27, 2021

(87) PCT Pub. No.: WO2020/259214
PCT Pub. Date: Dec. 30, 2020

(65) Prior Publication Data
US 2022/0265537 A1    Aug. 25, 2022

(30) Foreign Application Priority Data

Jun. 28, 2019 (WO) ................ PCT/CN2019/093593
Dec. 6, 2019 (WO) ................ PCT/CN2019/123550
Dec. 6, 2019 (WO) ................ PCT/CN2019/123572

(51) Int. Cl.
| | |
|---|---|
| *A61Q 5/10* | (2006.01) |
| *A61K 8/49* | (2006.01) |
| *A61K 8/22* | (2006.01) |
| *A61K 8/34* | (2006.01) |
| *A61K 8/41* | (2006.01) |
| *A61K 8/46* | (2006.01) |
| *A61K 8/23* | (2006.01) |
| *A61K 8/44* | (2006.01) |
| *A61K 8/67* | (2006.01) |
| *A61K 8/81* | (2006.01) |
| *A61K 8/04* | (2006.01) |

(52) U.S. Cl.
CPC ............. *A61K 8/494* (2013.01); *A61K 8/046* (2013.01); *A61K 8/22* (2013.01); *A61K 8/23* (2013.01); *A61K 8/347* (2013.01); *A61K 8/411* (2013.01); *A61K 8/415* (2013.01); *A61K 8/447* (2013.01); *A61K 8/46* (2013.01); *A61K 8/4926* (2013.01); *A61K 8/4953* (2013.01); *A61K 8/676* (2013.01); *A61K 8/8147* (2013.01); *A61K 8/8158* (2013.01); *A61Q 5/10* (2013.01); *A61K 2800/4324* (2013.01); *A61K 2800/48* (2013.01); *A61K 2800/522* (2013.01); *A61K 2800/5424* (2013.01); *A61K 2800/882* (2013.01)

(58) Field of Classification Search
CPC .......... A61K 8/494; A61K 8/046; A61K 8/22; A61K 8/23; A61K 8/347; A61K 8/411; A61K 8/415; A61K 8/447; A61K 8/46; A61K 8/4926; A61K 8/4953; A61K 8/676; A61K 8/8147; A61K 8/8158; A61K 2800/4324; A61K 2800/48; A61K 2800/522; A61K 2800/5424; A61Q 5/10
USPC ............................................................ 8/405
See application file for complete search history.

(56) References Cited

U.S. PATENT DOCUMENTS

| | | | |
|---|---|---|---|
| 3,413,072 A | 11/1968 | Ghilardi et al. | |
| 5,520,706 A * | 5/1996 | Samain ............... | A61K 8/19 8/408 |
| 7,150,765 B2 * | 12/2006 | Desenne ............ | A61Q 5/10 8/408 |
| 7,402,180 B2 * | 7/2008 | Vuarier ............... | A61Q 5/10 8/408 |
| 2003/0074747 A1 * | 4/2003 | Vuarier ............... | A61Q 5/10 8/405 |
| 2003/0226217 A1 | 12/2003 | Bowes et al. | |
| 2006/0117498 A1 | 6/2006 | Bureiko et al. | |
| 2010/0192969 A1 * | 8/2010 | DeGeorge ........... | A61K 8/411 8/421 |
| 2011/0203605 A1 * | 8/2011 | Allard ................. | A61Q 5/08 206/581 |
| 2011/0209720 A1 * | 9/2011 | DeGeorge ........... | A61Q 5/10 132/208 |
| 2019/0191844 A1 * | 6/2019 | Dreher ............... | A46B 11/0072 |

FOREIGN PATENT DOCUMENTS

| | | | | |
|---|---|---|---|---|
| CN | 105555251 B | * | 4/2019 | ............ A61Q 5/10 |
| CN | 109718124 A | | 5/2019 | |
| DE | 23 59 399 A1 | | 6/1975 | |
| DE | 38 43 892 A1 | | 6/1990 | |
| DE | 41 33 957 A1 | | 4/1993 | |
| DE | 195 43 988 A1 | | 5/1997 | |
| EP | 0 770 375 A1 | | 5/1997 | |

(Continued)

OTHER PUBLICATIONS

International Search Report dated Aug. 27, 2020 in PCT/CN2020/093636, citing documents AO through AQ therein, 2 pages.
French Search Report dated Mar. 25, 2021 in French Patent Application No. 2007576 (with English translation of Category of Cited Documents), citing documents AA through AC, AR through Au and AX through AZ therein, 4 pages.
Database GNPD [Online] MINTEL: Nov. 9, 2001 (Nov. 9, 2011), anonymous: "Graphite Black Hair Color", XP055788581, Database accession No. 10096261, 3 pages.
Database GNPD [Online] MINTEL: Jul. 16, 2001 (Jul. 16, 2011), anonymous: "Féria Hair Colourant", XP055788582, Database accession No. 106797, 2 pages.

(Continued)

*Primary Examiner* — Eisa B Elhilo
(74) *Attorney, Agent, or Firm* — Oblon, McClelland, Maier & Neustadt, L.L.P.

(57) ABSTRACT

A dye kit comprising: (A) a dyeing composition (A) and (B) a pyrazolone composition (B) comprising a retarding combination of pyrazolone compound and a reducer.

14 Claims, No Drawings

(56) References Cited

FOREIGN PATENT DOCUMENTS

| | | |
|---|---|---|
| FR | 2 586 913 A1 | 3/1987 |
| FR | 2 733 749 A1 | 11/1996 |
| FR | 2 801 308 A1 | 5/2001 |
| GB | 1026978 | 4/1966 |
| GB | 1153196 | 5/1969 |
| JP | 2-169571 A | 6/1990 |
| JP | 5-63124 A | 3/1993 |
| JP | 2013-112641 A | 6/2013 |
| WO | WO 94/08969 A1 | 4/1994 |
| WO | WO 94/08970 A1 | 4/1994 |
| WO | WO 96/15765 A1 | 5/1996 |
| WO | WO 2006/060568 A1 | 6/2006 |
| WO | WO 2013/004786 A2 | 1/2013 |
| WO | WO 2015/198923 A1 | 12/2015 |
| WO | WO 2019/125788 A1 | 6/2019 |
| WO | WO 2020/258731 A1 | 12/2020 |
| WO | WO 2020/259214 A1 | 12/2020 |

OTHER PUBLICATIONS

Zviak Charles: "Science des traitement capillaires", Science des Traitements Capiliaires, Masson Paris, FR Jan. 1, 1988 (Jan. 1, 1988), pp. 271-273 XP002467880.
Indian Office Action dated Jun. 27, 2022 in Indian Patent Application No. 202247004146, 5 pages.
European Search Report dated Aug. 1, 2023, in Application No. 20832588.
Database GNPD [Online] MINTEL; Sep. 18, 2015, anonymous: "Permanent Hair Colour Cream", XP055788124, Database accession No. 3351843 *abstract*, 4 pages.

* cited by examiner

COMPOSITION FOR DYEING KERATIN FIBRES AND USE THEREOF

TECHNICAL FIELD

The present invention relates to a composition for dyeing keratin fibres, in particular human keratin fibres such as hair.

BACKGROUND

Many people have for a long time sought to modify the colour of their hair, and especially to dye it in order, for example, to mask their grey hair.

"Permanent" dyeing methods also known as oxidative dyeing, which use colorant compositions containing oxidative dye precursors, generally referred to as oxidation bases, such as ortho- or para-phenylenediamines, ortho- or para-aminophenols and heterocyclic compounds, have been developed for dyeing human keratin fibres in a long-lasting manner. These oxidation bases are colourless or weakly coloured compounds, which, when combined with oxidizing products, may give rise to coloured compounds via a process of oxidative condensation.

The dyeing product can comprise both at least one oxidative dye and at least one oxidant. For better use, the oxidative dye and the oxidant may be placed respectively in a multi-compartment package, and are mixed together immediately before use.

Consumers desire using dyes for dyeing only the target area. However, in many cases, e.g., when dyeing hair, some other areas may be undesiredly dyed (stained), such as hand, face, ear and the like. Consumers have to pay more attention to avoid the undesired areas, and have been seeking for products help them to remedy the undesired dyeing. Various antioxidants are used in products for various purposes. However, it is still unknown that which component(s) can, and how to, achieve the effective avoidance of undesired stain by dye at a technically acceptable level, e.g., sufficient avoidance of stain, balance between avoidance of stain and effective dyeing, and so on. Further, for many antioxidants or other usefully active components, the stability thereof, especially stability over time, is one of the predominant challenges in the art.

SUMMARY OF THE INVENTION

The inventors have now discovered that the use of a specific retarding combination of a retardant and a reducer, together with an oxidative dye makes it possible to obtain a composition for the oxidative dyeing of keratin fibres, which can overcome the above drawbacks, especially reducing or even substantially avoiding of undesired stain by dye to a non-target position. In addition, the specific retarding combination shows excellent stability, e.g., minimized loss of amount of the subject component(s) over time.

One subject of the present invention is thus a dye kit for the oxidative dyeing of keratin fibres comprising:
  (A) a dyeing composition (A); and
  (B) a pyrazolone composition (B) comprising a retarding combination of a pyrazolone compound and a reducer.
Optionally, the pyrazolone composition (B) is placed in a chamber separate from the dyeing composition (A).
According to an embodiment of the invention, the dyeing composition (A) may in turn comprise:
  (I) a colorant composition (I), comprising:
    i) at least one oxidative dye(s); and
  (II) a developer composition (II), comprising:
    ii) at least one developer.
Optionally, the pyrazolone composition (B) comprising a retarding combination of a pyrazolone compound and a reducer is placed in the composition (I).

The present invention provides a retarding combination of a pyrazolone compound and a reducer, which can be used to slow down reactions of dye or intermediates thereof.

The present invention thus provides use of the retarding combination of a pyrazolone compound and a reducer, used as a retardant, for slowing down reactions of dye or intermediates thereof.

The present invention also provides use of the retarding combination for reducing stain of a dye.

The present invention also relates to a process for dyeing keratin fibres, in particular human keratin fibres such as the hair, using the dye kit according to the invention.

The present invention also relates to a process of slowing down reactions of dye or intermediates thereof, characterized in mixing the retarding combination with the dye. Preferably, the retarding combination is mixed with the dye before application of the dye, or the retarding combination is applied to the position to which the dye has been applied for less than 10 minutes, less than 5 minutes, or less than 3 minutes.

EMBODIMENTS OF THE INVENTION

Throughout the description, including the claims, the term "comprising a" should be understood as being synonymous with "comprising at least one", unless otherwise mentioned. Moreover, the expression "at least one" used in the present description is equivalent to the expression "one or more".

Throughout the description, including the claims, an embodiment defined with "comprising" or the like should be understood to encompass a preferable embodiment defined with "consisting substantially of" and a preferable embodiment defined with "consisting of".

Throughout the description, including the claims, the "keratin fibre" according to the present invention is the hair, eyelashes, eyebrows, or bodily hair. Preferably, the keratin fibre according to the present invention is hair.

In the application, unless specifically mentioned otherwise, contents, parts and percentages are expressed on a weight basis.

Throughout the description, including the claims, the term "retardant" means an agent capable of slowing down reactions of dye or intermediates thereof, such as the reactions with developer, e.g., an oxidation reaction therebetween. For the purpose of the present invention, "retarding combination" or the like may be interchangeably used with "retardant".

According to the present invention, "reducing the stain" refers to the reduction of stain occurring in undesired areas, such as hands, face, scalp, ears, rinsing water, towels, floor, and the like. Preferably, the effect lasts at least 5 minutes after the dyeing of the hair, more particularly 10 minutes, even more preferably 15 minutes, or 20 minutes.

One subject of the present invention is to provide a retarding combination, useful for slowing down reactions of dye or intermediates thereof, consisting of:
  a pyrazolone compound, and
  a reducer.

One subject of the present invention is to provide a dye kit for the oxidative dyeing of keratin fibres, comprising:
(A) a dyeing composition (A), comprising:
(I) a colorant composition (I), comprising:
i) at least one oxidative dye(s); and
and
(B) a pyrazolone composition (B) comprising a retarding combination of a pyrazolone compound and a reducer.

The dye kit according to the present invention can further comprise: (II) a developer composition (II), comprising ii) at least one oxidant.

The dye kit of the invention is intended to be used in a process for dyeing keratin fibres.

A subject of the invention is thus a process of dyeing keratin fibres, which consists in mixing the colorant composition (I) with the composition (II) of the dyeing composition (A) immediately before use to obtain a dye mixture, optionally adding the pyrazolone composition (B) comprising a retarding combination of a pyrazolone compound and a reducer into the dye mixture, and applying to the keratin fibres the dye kit of the invention.

In a variant embodiment according to the present invention, a pyrazolone compound can be added directly into the colorant composition (I).

Other characteristics and advantages of the invention will emerge more clearly on reading the description and the examples that follow.

Other than in the operating examples, or where otherwise indicated, all numbers expressing quantities of components and/or reaction conditions are to be understood as being modified in all instances by the term "about," meaning within 10% of the indicated number (e.g. "about 10%" means 9%-11% and "about 2%" means 1.8%-2.2%).

The dyeing composition (A) placed in the kit according to the present invention comprises a colorant composition (I) and a developer composition (II).

According to an embodiment of the present invention, the colorant composition (I) and the developer composition (II) can be used at a ratio by weight of 1:3 to 3:1, preferably 1:2 to 2:1, or preferably 2:3 to 1:1.

Colorant Composition (I)

The dyeing composition (A) placed in the kit according to the present invention comprises a colorant composition (I).

The colorant composition (I) of the composition (A) according to the present invention can comprise at least one oxidative dye(s).

Oxidative Dye

As indicated previously, the colorant composition (I) according to the invention comprises one or more oxidative dyes for use as component i).

The oxidative dyes that may be used in the present invention are generally chosen from oxidation bases, combined with one or more couplers.

Preferentially, the oxidative dye(s) comprise one or more oxidation bases.

The oxidation bases may be chosen especially from para-phenylenediamines, bis(phenyl)alkylenediamines, para-aminophenols, ortho-aminophenols, heterocyclic bases, and the addition salts thereof, and mixtures thereof.

Among the para-phenylenediamines, an unsubstituted para-phenylenediamine or a para-phenylenediamine substituted with 1 or 2 C1-C4 alkyl is preferred. Among others, examples that may be mentioned include para-phenylenediamine, 2-chloro-para-phenylenediamine, 2-methyl-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine. Other para-phenylenediamines may also be used, for example, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols, an unsubstituted para-aminophenol or a para-aminophenol substituted with 1 or 2 C1-C4 alkyl is preferred. Among others, examples that may be mentioned include para-aminophenol, 4-amino-3-methylphenol, and 4-amino-2-methylphenol. Other para-phenylenediamines may also be used, for example, 4-amino-3-fluorophenol, 4-amino-3-chlorophenol, 4-amino-3-hydroxymethylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1, 5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diaminopyrazole, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

4,5-diaminopyrazoles will preferably be used, e.g., 4,5-diamino-1-hydroxy C1-C4 alkylpyrazole, and even more preferentially 4,5-diamino-1-(β-hydroxyethyl)pyrazole and/or a salt thereof, especially a sulphate thereof.

The oxidative dye(s) may also comprise one or more couplers, which may be chosen from those conventionally used for the dyeing of keratin fibres.

Among these couplers, mention may be made especially of meta-phenylenediamines, meta-aminophenols, meta-diphenols, naphthalene-based couplers, heterocyclic couplers, and also the addition salts thereof, and mixtures thereof. In particular, unsubstituted meta-aminophenol or a meta-aminophenol substituted with 1 or 2 C1-C4 alkyl, unsubstituted meta-diphenol or a meta-diphenol substituted with 1 or 2 C1-C4 alkyl, diamino-phenols, or unsubstituted hydroxyindoles, an amino substituted hydroxypyridine, or hydroxybenzomorpholine can be preferably used.

Examples that may be mentioned include 1-hydroxy-3-aminobenzene, 1-methyl-2-hydroxy-4-aminobenzene, 1,3-dihydroxybenzene, 1,3-dihydroxy-2-methylbenzene, 5-amino-6-chloro-o-methylphenol, 2-methyl-5-hydroxyethylaminophenol, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof, such as chlorhydrate or dichlorhydrate thereof, e.g., 1-beta-hydroxyethyloxy-2,4-diamino-benzene dichlorhydrate (2,4-diaminophenoxyethanol HCl).

In general, the addition salts of the oxidation bases and couplers that may be used within the context of the invention are especially chosen from the addition salts with an acid such as the hydrochlorides, hydrobromides, sulfates, citrates, succinates, tartrates, lactates, tosylates, benzenesulfonates, phosphates and acetates.

In a first exemplary embodiment for oxidation base, examples comprise unsubstituted para-phenylenediamine or a para-phenylenediamine substituted with 1 or 2 C1-C4 alkyl.

In a second exemplary embodiment for oxidation base, examples comprise an unsubstituted para-aminophenol or a para-aminophenol substituted with 1 or 2 C1-C4 alkyl, in particular an unsubstituted para-aminophenol.

In a third exemplary embodiment for oxidation base, examples comprise 4,5-diaminopyrazoles will preferably be used, e.g., 4,5-diamino-1-hydroxy C1-C4 alkylpyrazole, or a salt thereof.

For the oxidation base, the unsubstituted para-aminophenol or a para-aminophenol substituted with 1 or 2 C1-C4 alkyl is particularly mentioned.

In particular, for coupler, unsubstituted meta-aminophenol or a meta-aminophenol substituted with 1 or 2 C1-C4 alkyl, unsubstituted meta-diphenol or a meta-diphenol substituted with 1 or 2 C1-C4 alkyl, diamino-phenols, or unsubstituted hydroxyindoles, an amino substituted hydroxypyridine, or hydroxybenzomorpholine can be preferably used.

When unsubstituted hydroxyindoles, an amino substituted hydroxypyridine, or hydroxybenzomorpholine is used as coupler, it is preferably used in combination with the oxidation base according to the second exemplary embodiment.

When an oxidation base according to the third exemplary embodiment for oxidation base is used, it is preferably used in combination with an amino substituted hydroxypyridine as a coupler.

In addition, the combination of 2-amino-3-hydroxypyridine as a coupler with the oxidation base according to the second exemplary embodiment, or the combination of 5-amino-6-chloro-o-methylphenol as a coupler with the oxidation base according to the second exemplary embodiment, can be individually mentioned.

Amongst others, the combination of 4,5-diamino-1-(β-hydroxyethyl)pyrazole sulphate as an oxidation base with the 2-amino-3-hydroxypyridine as a coupler, is particularly mentioned.

The oxidation base(s) may advantageously represent from 0.0001% to 10% by weight relative to the total weight of the composition (I), preferably from 0.005% to 5% by weight and better still from 0.1% to 5% by weight.

The coupler(s), if they are present, may advantageously represent from 0.0001% to 10% by weight relative to the total weight of the composition (I), and preferably from 0.005% to 5% by weight.

Antioxidant

The colorant composition (I) can comprise an antioxidant.

The antioxidants used may include natural exogenous phytochemical antioxidants such as phenols and carotenoids.

The antioxidant can include flavonoids. Flavonoids constitute a large class of more than 5,000 polyphenolic phytochemicals with antioxidant properties that act by direct free radical scavenging. Flavonoids have anti-inflammatory, antibacterial, antiviral, anti-allergic, anti-mutagenic, anti-thrombotic, anti-tumor and vasodilating effects and these methods of action can also be used to prevent, alleviate or eliminate oxidative damage from dental instruments. Flavonoids also exhibit chelation properties with metal ions and can mitigate oxidative damage from metal ions by chelating ions. The formation and stability of flavonoid-metal chelate is dependent on the function of the structure. Flavonoids having a catechol moiety and having a hydrogen bond between the hydroxyl groups at the 5-position and the 3-position have chelation properties.

Vitamin C and derivatives can be used, including ascorbic acid, erythorbic acid, or derivatives thereof, e.g., sodium ascorbate/erythorbate and the fat-soluble ester tetrahexyl decyl ascorbate/erythorbate and ascorbyl palmitate, magnesium ascorbyl phosphate, ascorbyl glucoside, glucosamine ascorbate, ascorbyl acetate, and the like. In addition, it is also possible to use plants derived from a large amount of vitamin C, such as extracts of Myrciaria dubia, acerola, emblica officinalis, and bioflavonoids from rose hips and citrus, including Water-soluble bioflavonoids such as hesperidin methyl chalcone.

Sesamum indicum or lignan may also be added. Sesame and its lignans (fibrous compounds associated with sesame) act as antioxidants. Sesame seed lignan significantly enhances vitamin E activity.

Other antioxidants which may be incorporated into the compositions of the present invention include tocopherols (e.g., d-alpha-tocopherol, d-beta-tocopherol, d-gamma-tocopherol, d-delta-tocopherol), tocotrienol Phenol (eg d-α-tocotrienol, d-β-tocotrienol, d-γ-tocotrienol, d-δ-tocotrienol) and vitamin E (α-tocopheryl acetate)). These compounds can be isolated from natural sources, prepared by synthetic means or mixed. The tocotrienol-rich vitamin E preparation can be obtained by fractionating the vitamin E preparation to remove a portion of the biophenol and recovering the higher concentrated tocotrienol product. Useful tocotrienols are natural products isolated, for example, from wheat germ oil, grain or palm oil using high performance liquid chromatography or from barley, distiller's grains or oats by alcohol extraction and/or molecular distillation. The term "tocotrienol" as used herein includes a tocotrienol-rich fraction obtained from these natural products as well as a pure compound. Increased glutathione peroxidase activity protects the skin from oxidative damage.

In addition, carotenoids, especially lutein types, are also useful antioxidants that can be used. Lutein-type carotenoids include molecules such as lutein, canthaxantin, cryptoxanthin, zeaxanthin and astaxanthin. Lutein compounds protect compounds such as vitamin A, vitamin E and other carotenoids.

The flavonoid may be a flavanone (a derivative of 2,3-dihydro-2-phenylbenzopyran-4-one). Flavanones include: scutellarin, eriodictin, hesperetin, hesperidin, sylvestre, iso-sakuranetin, naringenin, naringin, pinocin, tangrin (poncirin)), sakuranetin, sakura glycosides and 7-O-methyl ergophenol (Sterubin).

The flavonoid may be a dihydroflavonol (a derivative of 3-hydroxy-2,3-dihydro-2-phenylbenzopyran-4-one). Flavanols include: taxifolin, Aromadedrin, Chrysandroside A, Chrysandroside B, Xeractinol, astilbin, and flavonol.

The flavonoid may be a flavonoid (a derivative of 2-phenylbenzopyran-4-one). Flavonoids include: Apigenin, luteolin, tangeritin, Chrysin, baicalein, wild baicalein, wogonin, synthetic flavonoids: Diosmin and flavonoids ester.

The flavonoid may be a flavonol (a derivative of 3-hydroxy-2-phenylbenzopyran-4-one). Flavonols include: 3-hydroxyflavone, rhodoxanthin, quercetin, galangin, cotton dermatan, kaempferol, kaempferol, isorhamnetin, mulberry pigment, myricetin, naringin (Natsudaidain), Muskyl flavonol (Pachypodol), quercetin, methyl rhamnosin, rhamnetin, azalein, hyperoside, isoquercetin, kaempferol, myricetin, suede Glycosides, Robinin, Rutin, Spiraea, Xanthorhamnin, Amurensin, Icariin and Tracuridine.

The flavonoid may be a flavan-3-ol (a derivative of 2-phenyl-3,4-dihydro-2H-benzopyran-3-01). Flavan-3-ol includes: catechin, epicatechin, epigallocatechin, epicatechin gallate, epigallocatechin gallate, epiafzelechin, Fisetinidol, Guibourtinidol, Mesquitol and Robinetinidol.

The flavonoid may be a flavan-4-ol (a derivative of 2-phenylchroman-4-ol). Flavan-4-ols include: Apiforol and Luteoforol.

The flavonoid may be an isoflavone (a derivative of 3-phenylbenzopyran-4-one). Isoflavones include: genistein, daidzein, garbanin A, formononetin, and equol metabolites from daidzein.

The antioxidant may be anthocyanin (a derivative of 2-phenylbenzopyranoside cation). Anthocyanins include: Aurantinidin, cyanidin, delphinidin, Europinidin, Luteolinidin, Pelargonidin, Malvidin, Peonyidin (Peonidin)), morning glory pigment (Petunidin), rose pigment (Rosinidin) and xanthone.

The antioxidant may be dihydrochalcone (a derivative of 1,3-diphenyl-1-propanone). Dihydrochalcone includes: phloretin, dihydrochalcone phloridin cisplatin, Aspalathin, naringin dihydrochalcone, neohesperidin dihydrochalcone and Nothofagin. The mode of action of the present invention is not limited, but dihydrochalcone can exert an antioxidant effect by reducing active radicals such as active oxygen and reactive nitrogen species.

The antioxidant can be anthocyanin. Anthocyanins and their derivatives are antioxidants. Anthocyanins comprise a class of flavonoid compounds responsible for the red, purple and blue colors of many fruits, vegetables, grains and flowers, which are naturally occurring water-soluble compounds. In addition, anthocyanins are collagenase inhibitors. Inhibition of collagenase helps prevent and reduce wrinkles caused by skin collagen reduction, increase skin elasticity, and the like. Anthocyanins can be obtained from any part of a variety of plant sources, such as solids, flowers, stems, leaves, roots, bark or seeds. Those skilled in the art will appreciate that certain portions of the plant may contain higher natural levels of anthocyanins, and thus these moieties are used to obtain the desired anthocyanins. In some cases, the antioxidant can include one or more betaine. Betatin, similar to anthocyanins, is available from natural sources and is an antioxidant.

The antioxidant may be a phenylpropanoid (a derivative of cinnamic acid). Phenylpropanoids include: cinnamic acid, caffeic acid, ferulic acid, trans-ferulic acid (including its antioxidant pharmacore 2,6-dihydroxy acetophenome), 5-hydroxyferic acid, sinapic acid, Coumarin, coniferyl alcohol, sinapyl alcohol, eugenol, Chavicol, baicalein, P-coumaric acid and sinapinic acid. Without limiting the mode of action of the present invention, phenylpropanoids can neutralize free radicals.

The antioxidant may be chalcone (a derivative of 1,3-diphenyl-2-propen-1-one). Chalcone includes: zirconia, Okanin, safflower, Marein, Sophoradin, Xanthohumol, Flavokvain A, Flavokavain B, Flavokavin C and Synthetic Safalcone.

The antioxidant may be curcuminoid. Curcuminoids include: curcumin, demethoxycurcumin, bis-demethoxycurcumin, tetrahydrocurcumin, and tetrahydrocurcumin. Curcumin and tetrahydrocurcumin can be derived from the rhizome of turmeric. Tetrahydrocurcumin, a metabolite of curcumin, has been found to be a more potent antioxidant and more stable than curcumin.

The antioxidant can be tannin. Tannins include: tannins, Terflavin B, Glucogallin, Dgallic acid, and Quercitannic acid.

The antioxidant can be a stilbenoid. The mites include: resveratrol, red sandalwood and paclitaxel. Resveratrol can include, but is not limited to, 3,5,4'-trihydroxyindole, 3,4,3',5'-tetrahydroxyindole (cetotriol), 2,3',4,5'-Tetrahydroxyindole (oxidized resveratrol), 4,4'-dihydroxyindole and its alpha and beta glucoside, galactoside and mannoside derivatives.

The antioxidant may be coumarin (a derivative of 2H-benzopyran-2-one). Coumarins include: 4-hydroxycoumarin, umbelliferone, Aesculetin, Herniarin, Auraptene, and dicoumarin.

The antioxidant can be a carotenoid. Carotenoids include: beta-carotene, alpha-carotene, gamma-carotene, beta-cryptoxanthin, lycopene, lutein and idebenone.

The antioxidant can be a vitamin of a derivative thereof. Vitamins include: retinol, ascorbic acid or erythorbic acid, L-ascorbic acid, tocopherol, tocotrienol and vitamin cofactor: coenzyme Q10.

The antioxidant may be: xanthone, butylated hydroxytoluene, 2,6-di-tert-butylphenol, 2,4-dimethyl-6-tert-butylphenol, gallic acid, eugenol, uric acid, α-lipoic acid, ellagic acid, cichoric acid, chlorogenic acid, rosmarinic acid, salicylic acid, acetylcysteine, S-allylcysteine, pyridone (Barbigerone), Chebulagic acid, edaravone, ethoxyquin, glutathione, hydroxytyrosol, idebenone, melatonin, N-acetyl serotonin, nordihydroguaiac Acid, Oleotanthal, oleuropein, Paradol, paclitaxel, probucol, propyl gallate, protocatechuic acid, pyrithione, rutin, flax lignan diglucoside, sesamin, sesame phenol, Silybin, silymarin, theaflavins, theaflavins digallate, Thmoquinone, Trolox, tyrosol, polyunsaturated fatty acids and sulfur-based antioxidants such as methionine or lipoic acid.

The antioxidant, including the reducer, described above is preferably used according to the invention in an amount which may range from 0.001 to 10% by weight, preferably from 0.1 to 7% by weight, more preferably from 0.5 to 5% by weight, relative to the total weight of the colorant composition (I).

Surfactant

The colorant composition (I) according to the invention may comprise one or more surfactant(s), e.g., in particular anionic surfactant and/or non-ionic surfactant.

Anionic Surfactant

The colorant composition (I) according to the invention may further comprise one or more anionic surfactant(s).

The term "anionic surfactant" means a surfactant comprising, as ionic or ionizable groups, only anionic groups. These anionic groups are preferably chosen from the following groups:

—COOH, —COO$^-$, —SO$_3$H, —SO$_3^-$, —OSO$_3$H, —PO$_2$H$_2$, —PO$_2$H$^-$, —P(OH)$_2$, =P(O)OH, —P(OH)O$^-$, =P(O)O$^-$, =POH, =PO$^-$, the anionic parts comprising a cationic counterion such as an alkali metal, an alkaline-earth metal or an ammonium.

As examples of anionic surfactants that may be used in the colorant composition (I) according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids, and the corresponding non-salified forms of all these compounds; the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts, or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Preferred anionic surfactants are chosen from ($C_6$-$C_{30}$) alkyl sulfates, ($C_6$-$C_{30}$)alkyl ether sulfates, ($C_6$-$C_{30}$)alkylamido ether sulfates, alkylaryl polyether sulfates and monoglyceride sulphates, all these compounds optionally comprising from 1 to 20 ethylene oxide units; and more preferably from ($C_{12}$-$C_{20}$)alkyl sulphates and ($C_{12}$-$C_{20}$)alkyl ether sulfates comprising from 2 to 20 ethylene oxide units, and even more preferably from 1 to 4 ethylene oxide units, especially in the form of alkali metal, ammonium, amino alcohol and alkaline-earth metal salts, or a mixture of these compounds. Better still, it is preferred to use a polyoxyethylenated sodium lauryl ether sulphate, such as sodium lauryl ether sulphate containing 2 or 2.2 mol of ethylene oxide.

Preferably, the anionic surfactants of the invention are sulfates, more specifically is chosen from ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates and monoglyceride sulfates, their salts such as alkali salts, such as sodium, and their mixtures.

More preferably the anionic surfactants of the invention are chosen from ($C_6$-$C_{30}$)alkyl sulfates, ($C_6$-$C_{30}$)alkyl ether sulfates, particularly $(C_6-C_{30})$alkyl ether sulfates such as lauryl ether sulfate, their salts, such as sodium laureth sulfate.

The amount of said anionic surfactant(s) in the colorant composition (I) according to the invention is 0.01 to 10% by weight, with regard to the total weight of the composition (I).

Non-Ionic Surfactant

The colorant composition (I) according to the invention may further contain one or more non-ionic surfactant(s).

The nonionic surfactant(s) that may be used in the compositions are described, for example, in the *Handbook of Surfactants* by M. R. Porter, published by Blackie & Son (Glasgow and London), 1991, pp. 116-178.

Examples of nonionic surfactants that may be mentioned include the following nonionic surfactants:

oxyalkylenated $(C_8-C_{24})$alkylphenols;
saturated or unsaturated, linear or branched, oxyalkylenated or glycerolated $C_8-C_{40}$ alcohols, comprising one or two fatty chains;
saturated or unsaturated, linear or branched, oxyalkylenated $C_8-C_{30}$ fatty acid amides;
esters of saturated or unsaturated, linear or branched, $C_8-C_{30}$ acids and of polyethylene glycols;
esters of saturated or unsaturated, linear or branched, $C_8-C_{30}$ acids and of sorbitol, preferably oxyethylenated;
fatty acid esters of sucrose;
$(C_8-C_{30})$alkyl(poly)glucosides, $(C_8-C_{30})$alkenyl(poly)glucosides, which are optionally oxyalkylenated (0 to 10 oxyalkylene units) and comprising from 1 to 15 glucose units, $(C_8-C_{30})$alkyl (poly)glucoside esters;
saturated or unsaturated, oxyethylenated plant oils;
condensates of ethylene oxide and/or of propylene oxide, inter alia, alone or as mixtures;
N—$(C_8-C_{30})$alkylglucamine and N—$(C_8-C_{30})$ acylmethylglucamine derivatives;
aldobionamides;
amine oxides;
oxyethylenated and/or oxypropylenated silicones;
and mixtures thereof.

The terms "oxyalkylenated", "oxyethylenated", "oxypropylenated" and "glycerolated" cover, respectively, mono- or poly-oxyalkylenated, oxyethylenated, oxypropylenated and glycerolated compounds, unless specifically mentioned.

The oxyalkylene units are more particularly oxyethylene or oxypropylene units, or a combination thereof, preferably oxyethylene units.

The number of moles of ethylene oxide and/or propylene oxide preferably ranges from 1 to 250, more particularly from 2 to 100 and better still from 2 to 50; the number of moles of glycerol ranges especially from 1 to 50 and better still from 1 to 10.

Advantageously, the nonionic surfactants according to the invention do not comprise any oxypropylene units.

As examples of glycerolated nonionic surfactants, use is preferably made of monoglycerolated or polyglycerolated $C_8-C_{40}$ alcohols, comprising from 1 to 50 mol of glycerol and preferably from 1 to 10 mol of glycerol.

As examples of compounds of this type, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

Among the glycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The additional nonionic surfactant(s), when they are present in the colorant composition (I) according to the invention, are preferably present in a total amount ranging from 0.01 to 1% by weight, with regard to the total weight of the composition.

Solvent

The colorant composition (I) according to the invention can advantageously comprise one or more solvent(s), e.g., water and/or organic solvent.

Water

The colorant composition (I) according to the invention advantageously comprises water.

The water content in the dye composition (I) according to the invention preferably ranges from 40% to 95% by weight, more preferentially from 50% to 90% by weight, or from 60% to 80% by weight, relative to the total weight of the composition (I).

Organic Solvent

The colorant composition (I) according to the invention may also comprise one or more water-soluble organic solvents (solubility of greater than or equal to 5% in water at 25° C. and at atmospheric pressure).

Examples of water-soluble organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as phenylethyl alcohol; polyols containing more than two hydroxyl functions, such as glycerol; polyol ethers, for instance ethylene glycol monomethyl, monoethyl and monobutyl ether, propylene glycol or ethers thereof, for instance propylene glycol monomethyl ether; and also diethylene glycol alkyl ethers, especially $C_1-C_4$ alkyl ethers, for instance diethylene glycol monoethyl ether or monobutyl ether, alone or as a mixture.

The water-soluble organic solvents, when they are present, generally represent between 1% and 20% by weight relative to the total weight of the colorant composition (I) according to the invention, and preferably between 3% and 15% by weight, or between 4% and 10% by weight.

Alkaline Agent

The colorant composition (I) according to the invention may further comprise one or more alkaline agents.

The alkaline agent(s) can especially be chosen from aqueous ammonia, alkali metal carbonates or bicarbonates, organic amines with a pKb at 25° C. of less than 12, in particular less than 10 and even more advantageously less than 6; from the salts of the amines mentioned previously with acids such as carbonic acid or hydrochloric acid: it should be noted that it is the pKb corresponding to the function of highest basicity.

Preferably, the composition (I) according to the present invention can be free of or substantially free of aqueous ammonia.

Preferably, the amines are chosen from alkanolamines, in particular comprising a primary, secondary or tertiary amine function, and one or more linear or branched $C_1-C_8$ alkyl groups bearing one or more hydroxyl radicals; from oxyethylenated and/or oxypropylenated ethylenediamines, and from amino acids and compounds having the following formula:

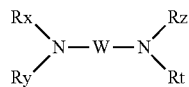

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

According to one embodiment of the invention, the colorant composition (I) according to the invention comprises at least one alkanolamine and/or at least one basic amino acid, more advantageously at least one alkanolamine, such as ethanolamine, or mixtures thereof.

Advantageously, the content of alkaline agent(s) ranges from 0.01% to 30% by weight, preferably from 0.1% to 20% by weight, or from 1% to 10% or 5% by weight relative to the total weight of the composition (I). It should be noted that this content is expressed as $NH_3$ when the alkaline agent is aqueous ammonia.

The pH of composition (I) of the invention is preferably 6-11, preferably 7-10, and more preferably 8-9.

The pH can be adjusted by adding acidifying agents, such as hydrochloric acid, (ortho)phosphoric acid, sulfuric acid, boric acid, and also carboxylic acids, for instance acetic acid, lactic acid or citric acid, or sulfonic acids. Alkaline agents such as those previously mentioned may also be used.

Fatty Phase

The colorant composition (I) according to the invention can comprise, moreover, a cosmetically acceptable fatty substance.

According to one particular embodiment, the fatty substance is free of carboxylic acid groups.

The term "fatty substance" means organic compounds that are insoluble in water at ordinary temperature (25° C.) and at atmospheric pressure (760 mmHg) (solubility of less than 5%, preferably 1% and even more preferentially 0.1%). They may preferably have in their structure a sequence of at least two siloxane groups or at least one hydrocarbon-based chain comprising at least 6 carbon atoms. In addition, the fatty substances are generally soluble in organic solvents under the same temperature and pressure conditions, for instance chloroform, ethanol, benzene or decamethylcyclopentasiloxane.

The fatty substances are especially chosen from lower alkanes, fatty alcohols, fatty acid esters, fatty alcohol esters, oils, in particular mineral, plant, animal or synthetic non-silicone oils, non-silicone waxes, and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which is (are) optionally substituted, in particular with one or more hydroxyl groups (in particular 1 to 4). If they are unsaturated, these compounds may comprise one to three conjugated or unconjugated carbon-carbon double bonds.

As regards lower alkanes, these alkanes comprise from 6 to 16 carbon atoms and are linear or branched, optionally cyclic. By way of example, the alkanes may be chosen from hexane and dodecane, isoparaffins such as isohexadecane and isodecane.

As non-silicone oils that may be used in the composition of the invention, examples that may be mentioned include:
hydrocarbon-based oils of animal origin, such as perhydrosqualene;
hydrocarbon-based oils of plant origin, such as liquid fatty acid triglycerides containing from 6 to 30 carbon atoms, for instance heptanoic or octanoic acid triglycerides, or alternatively, for example, sweet almond oil, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;
linear or branched hydrocarbons of more than 16 carbon atoms and of mineral or synthetic origin, such as liquid paraffins, petroleum jelly, liquid petroleum jelly, polydecenes, and hydrogenated polyisobutenes such as Parleam®;
fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition of the invention are not oxyalkylenated. They are saturated or unsaturated, linear or branched and comprise from 6 to 30 carbon atoms and more particularly from 8 to 30 carbon atoms. Mention may be made of cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The esters useful are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being more particularly greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still in the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may especially be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; ethylene glycol distearate; diethylene glycol distearate and polyethylene glycol distearate.

The composition may also comprise, as fatty ester, sugar esters and diesters of $C_6$-$C_{30}$ and preferably $C_{12}$-$C_{22}$ fatty acids. It is recalled that the term "sugar" means oxygenous hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, especially, oleo-palmitate, oleostearate and palmito-stearate mixed esters.

It is more particularly preferred to use monoesters and diesters and especially sucrose, glucose or methylglucose mono- or dioleates, stearates, behenates, oleopalmitates, linoleates, linolenates and oleostearates.

Advantageously, the content of fatty substance(s) ranges from 0.01% to 45% by weight, preferably from 0.1% to 30% by weight, or from 1% to 15% by weight relative to the total weight of the composition (I).

Adjuvants

The colorant composition (I) according to the invention may also comprise one or more cosmetic adjuvants.

For example, the composition (I) may comprise one or more additives that are well known in the art, such as anionic, nonionic or amphoteric polymers or mixtures thereof, agents for preventing hair loss, vitamins and provitamins including panthenol, the derivatives of these vitamins (in particular esters) and their mixtures; sunscreens, mineral or organic pigments, sequestrants, plasticizers, solubilizers, acidifying agents, opacifiers, hydroxy acids, nacreous agents, fragrances and preserving agents.

Needless to say, a person skilled in the art will take care to select this or these optional additional compound(s) such that the advantageous properties intrinsically associated with the invention are not, or are not substantially, adversely affected by the envisaged addition(s).

The above adjuvants may generally be present in an amount, for each of them, of between 0 and 20% by weight, or between 0 and 10% by weight, relative to the total weight of the composition (I).

The composition (I) according to the invention may be in the form of fluid or thickened liquids, gels or creams.

Developer Composition (II)

The dyeing composition (A) placed in the kit according to the present invention comprises a developer composition (II).

According to an embodiment of the present invention, the developer composition (II) is placed separate from the colorant composition (I).

Oxidant

The composition (II) of the composition (A) according to the present invention comprises at least one oxidant.

The developer composition (II) of the present invention may comprise one or more oxidant for generally use as one of the active components of the composition (II). The term "oxidant" is intended to mean an oxidant other than atmospheric oxygen. More particularly, the oxidant is selected from the group consisting of hydrogen peroxide, urea peroxide, alkali metal bromates, peroxy salts, such as persulfates or perborates, peracids and their precursors, and alkali or alkaline earth metals; or a polymer type complex capable of releasing hydrogen peroxide.

Advantageously, the oxidant is hydrogen peroxide.

The concentration of the oxidant may be from 0.1% by weight to 50% by weight, more preferably from 0.5% by weight to 20% by weight, still more preferably from 1% by weight to 15% by weight, based on the weight of the composition (II).

Solvent

The developer composition (II) of the present invention may comprise one or more solvent(s), e.g., water and/or organic solvent. The useful solvent can be selected from those discussed for the "solvent" of the composition (I) above.

The composition (I) and (II) of the dyeing composition (A) can independently use same or different solvents, respectively.

When water is used as a solvent in the developer composition (II) according to the invention, it is preferably used in a content of ranging from 40% to 95% by weight, more preferentially from 50% to 90% by weight, or from 60% to 85% by weight, relative to the total weight of the composition (II).

Examples of water-soluble organic solvents that may be mentioned include polyols containing more than two hydroxyl functions, such as glycerol.

The water-soluble organic solvents, when they are present, generally represent between 0.01% and 10% by weight relative to the total weight of the colorant composition (I) according to the invention, and preferably between 0.1% and 5% by weight.

Surfactant

The developer composition (II) according to the invention may comprise one or more surfactant(s), e.g., in particular anionic surfactant and/or non-ionic surfactant, preferably non-ionic surfactant. The useful surfactant can be selected from those discussed for the "surfactant" of the composition (I) above.

Chelating Agent

The colorant composition (I) and/or the developer composition (II) of dyeing composition (A) according to the present invention may comprise at least one chelating agent.

According to the present invention, the useful chelating agent comprises aminocarboxylic acids, e.g., ethylenediamine tetraacetic acid (EDTA), aminotriacetic acid, diethylene triaminepentaacetic acid, and in particular the alkali metal salt thereof, e.g., N,N-bis(carboxymethyl)glutamic acid, tetrasodium EDTA, tetrasodium salt of N,N-bis(carboxymethyl)glutamic acid (glutamic acid diacetic acid, GLDA); hydroxyl carboxylic acids, e.g., citric acid, tartaric acid, glucuronic acid, succinic acid, ethylenediamine disuccinic acid (EDDS), and in particular the alkali metal salt thereof; hydroxyl aminocarboxylic acids, e.g., hydroxyethylethylenediamine triacetic acid (HEDTA), dihydroxyethylglycine (DEG), and in particular the alkali metal salt thereof; polyphosphonic acid, and in particular the alkali metal salt thereof; other phosphor-containing organic acid, e.g., phytic acid, and in particular the alkali metal salt thereof, e.g., sodium phytate, potassium phytate polycarboxylic acid, e.g., polyacrylic acid, polymethacrylic acid, and in particular the alkali metal salt thereof.

In one embodiment, the at least one water soluble chelating agent is an alkali metal hydroxyl polycarboxylate represented by an alkane containing from 1 to 4 carbon atoms, preferably containing 2 or 3 carbon atoms, substituted by 1, 2, or 3 hydroxyl groups (—OH), preferably by one (1) hydroxyl group, and further substituted by 2, 3, 4 or 5 carboxylate groups (—COOM), preferably by 2 or 3 carboxylate groups (—COOM), wherein the multiple groups M independently represent H or alkali metal, with the proviso that at least one of the groups M represents alkali metal, such as Na, K or Li, preferably all groups M represent alkali metal, such as Na, K or Li, preferably Na. More specifically, the at least one alkali metal hydroxyl polycarboxylate may be chosen from sodium tartrates, sodium citrates, potassium tartrates, potassium citrates, and hydrates thereof, preferably sodium citrates, in particularly trisodium citrate. Herein, sodium citrates are used to indicate monosodium citrate, disodium citrate and trisodium citrate, and other alkali metal hydroxyl polycarboxylates may be understood in a similar way.

Amongst others, the alkali metal mentioned above is preferably sodium or potassium, in particular sodium. Accordingly, preferable chelating agents can comprise sodium citrate, tetrasodium EDTA, tetrasodium GLDA, trisodium EDDS, sodium phytate, or a mixture thereof.

In particular, the composition (I) and/or composition (II) of the present invention may comprise the at least one water soluble chelating agent in a content ranging from 0.01% to 1% by weight, especially from 0.1% to 0.4% by weight, relative to the total weight of the second composition.

Pyrazolone Composition (B)

In addition to the dyeing composition (A) comprising the colorant composition (I) and the developer composition (II), the dye kit according to the present invention may also comprise a pyrazolone composition (B) comprising a retarding combination of a pyrazolone compound and a reducer.

Pyrazolone Compound

The pyrazolone compound is preferably a pyrazolone substituted with at least one aryl and/or at least one alkyl, preferably C1-C4 alkyl; provided that the number of substituents aryl and alkyl is not more than 3. Preferably, the aryl is an unsubstituted phenyl or a phenyl substituted with at least one alkyl, preferably C1-C4 alkyl. For example, the pyrazolone compound can be a pyrazolone substituted with at least on phenyl and at least one C1-C4 alkyl, e.g., pyrazolone substituted with 1 phenyl and 1 methyl, pyrazolone substituted with 1 phenyl and 1 ethyl, and the like. Amongst others, mention may made to phenyl methyl pyrazolone (PMP), e.g., 3-methyl-1-phenyl-5-pyrazolone.

The pyrazolone compound in accordance with the invention are generally present in amounts ranging from 0.01% to 10% by weight, more preferably from even more preferably from 0.1% to 5% by weight and even more particularly from 0.3% to 3% by weight, or preferably from 0.5% to 2% by weight relative to the total weight of the composition (I) and/or the composition (II).

Reducer

The pyrazolone composition (B) can comprise a reducer, to protect the PMP and improve the stability thereof.

According to the present invention, useful reducers can comprise, sodium thiosulfate, sodium metabisulfite, thiourea sulfite ammonium, thioglycolic acid (TGA), thiolactic acid, ammonium thiolactate, mono-carbothioic acid diglycidyl ester, carbothioic ammonium acetate, thioglycerol, dithio glycolic acid, diammonium carbothioic strontium acetate, thio glycolate, carbothioic isooctyl, cysteine, cysteamine, homocysteine, glutathione peptide, thiomalic acid, 2-mercaptopropionic acid, 3-mercaptopropionic acid, thiodiglycol, 2-mercaptoethanol, dithiothreitol, thioxanthine, thiosalicylic acid thiopropionic acid, lipoic acid, N-acetylcysteine and its salts; ammonium thioglycolate, glycerol monothioglycolate, or a mixture thereof.

Example of preferred reducers that may be mentioned is a thio-organic acid, including thioglycolic acid, dithio glycolic acid, thiolactic acid, thiomalic acid, or a mixture thereof.

For the retarding combination, the reducer is used in an amount by weight more than that of the pyrazolone compound. For example, the reducer can be used at a weight ratio to the pyrazolone compound of 1.1:1 to 10:1, preferably 2:1 to 5:1.

Addition Form of the Pyrazolone Composition (B)

As stated above, the inventor has surprisingly discovered that the pyrazolone composition (B) comprising a retarding combination of a pyrazolone compound and a reducer can be used to slow down reactions of dye or intermediates thereof, e.g., the oxidative dye i) useful in the composition (I).

That is, the retarding combination acts mainly on the reaction of the dye. Accordingly, for the dye kit, the pyrazolone composition (B) can be added directly into the dyeing composition (A), e.g., as a mixture with the colorant composition (I); or can be added into an independent chamber, separate from the dyeing composition (A).

Accordingly, the present invention can advantageously provide a dyeing kit, comprising:

a dyeing composition (A) according to the present invention placed in chamber 1; and a pyrazolone composition (B) comprising a retarding combination of a pyrazolone compound and a reducer according to the present invention placed in chamber 2 separate from chamber 1.

Method and Use

One subject of the invention is a process for dyeing human keratin fibres, in particular the hair, using the dye kit as described above.

Another subject of the invention is a process for reducing the stain of a dye composition, using the dye kit as described above.

Another subject of the invention is a process for slowing down reactions of dye or intermediates, using the dye kit as described above.

The invention also relates to the use of the dye kit as described above for dyeing keratin fibres, in particular the hair.

The invention also relates to the use of the dye kit as described above for reducing the stain of the dye kit.

The invention also relates to the use of a dye kit as described above for slowing down reactions of dye or intermediates, using the dye kit as described above.

In particular, the invention relates to a process of slowing down reactions of dye or intermediates thereof, characterized in mixing a pyrazolone compound comprising phenyl methyl pyrazolone with the dye.

Preferably, the pyrazolone compound is mixed with the dye before application of the dye, or the pyrazolone compound is applied to the position to which the dye has been applied for less than 10 minutes, less than 5 minutes, or less than 3 minutes.

The present invention also relates to the use of a pyrazolone compound comprising phenyl methyl pyrazolone for reducing stain of a dye.

In another aspect, the present invention relates to the use of a composition for dyeing keratin fibers, while reducing the stain in areas other than the keratin fibers, wherein the composition comprises a pyrazolone compound comprising phenyl methyl pyrazolone.

According to a preferred embodiment, the dyeing process of the invention comprises mixing the colorant composition (I) and the composition (II) immediately before use, and applying the mixture obtained as described above to the keratin fibres.

More particularly, by "mixing" or a variant thereof, it is intended to mean the action of putting the colorant composition (I) of the present invention into a container or palm, together with the developer composition (II) as described above, with or without stirring them.

According to a preferred variant of the preferred embodiment, the colorant composition (I) of the present invention is put into a container or palm together with the developer composition (II) as described above, without stirring them.

Irrespective of the process used and the number of compositions used, the composition(s) described previously, optionally mixed beforehand, are applied to wet or dry keratin fibres.

As stated above in the portion of "Addition form of the pyrazolone composition (B)", the pyrazolone composition (B) can be provided in various forms to be used with the colorant composition (I) and the developer composition (II), so as to slow down the reaction of the dye. In particular, if the pyrazolone composition (B) is placed in chamber 2 separate from chamber 1, for the dye kit described according to the present invention:

- if the user does not want to slow down the dyeing, or the stain by dye is not cared, chamber 2 may not be used;
- if the user desires avoiding any stain, he/she can mix chamber 2 with 1 before dyeing;
- if the user wants to determine the use or not of chamber 2 depending on whether an actual stain occurs, he/she can firstly use only chamber 1, and when the dyeing composition is adhered to hand or anywhere else, chamber 2 may be immediately applied; and
- if the user wants to avoid stain, and desires rapid dyeing, he/she can apply in advance chamber 2 onto positions on which stain may most likely occur but should be avoided, e.g., hand.

Alternatively, if the pyrazolone composition (B) is provided together with the colorant composition (I), e.g., being added directly into the composition (I), the dyeing process is always slowed down, comparing with a same dyeing process except for the absence of the pyrazolone composition (B).

The mixed compositions, including the colorant composition (I) and the developer composition (II), and optionally the pyrazolone composition (B), are usually left in place on the fibres for a time generally ranging from 1 minute to 1 hour and preferably from 5 minutes to 30 minutes.

The temperature during the process is conventionally between 20 and 80° C. and preferably between 20 and 60° C. After the treatment, the human keratin fibres are advantageously rinsed with water. They may optionally be further washed with a shampoo, followed by rinsing with water, before being dried or left to dry.

The process may be repeated several times in order to obtain the desired coloration.

The abovementioned dye kit may also be equipped with means allowing the delivery to the hair of the desired mixture, such as, for example, the device described in patent FR 2 586 913.

The examples that follow are given purely as illustrations of the present invention.

EXAMPLES

The ingredient amounts/concentrations in the compositions/formulas described below are expressed in % by weight, relative to the total weight of each composition/formula.

Example 1

The colorant composition I-A and comparative composition I-B hereinafter were prepared, from the ingredients indicated in the table 1 below (in which the contents were indicated in wt % of materials with regard to the total weight of the composition):

TABLE 1

| Ingredients | I-A | I-B |
| --- | --- | --- |
| RESORCINOL | 0.8 | 0.8 |
| 2-METHYLRESORCINOL | 0.3 | 0.3 |
| SODIUM LAURETH SULFATE | 2 | 2 |
| p-AMINOPHENOL (and) SODIUM METABISULFITE | 0.5 | 0.5 |
| THIOGLYCOLIC ACID | 2 | 2 |
| CARBOMER | 0.7 | 0.7 |
| ETHANOLAMINE | 3.3 | 3.3 |
| GLYCERIN | 5 | 5 |
| PHENYL METHYL PYRAZOLONE | 0.5 | 0.5 |
| EDTA | 0.2 | 0.2 |
| TOLUENE-2,5-DIAMINE (and) THIOGLYCERIN | 2 | 2 |
| 2,4-DIAMINOPHENOXYETHANOL HCl | 0.15 | 0.15 |
| *PRUNUS DULCIS* | 0.01 | 0.01 |
| Water | QS | QS |

The developer composition II-A hereinafter was prepared, from the ingredients indicated in the table 2 below (in which the contents were indicated in wt % of materials with regard to the total weight of the composition):

TABLE 2

| Ingredients | II-A |
| --- | --- |
| Hydrogen peroxide | 12 |
| Tetrasodium etidronate | 0.2 |
| Tetrasodium pyrophosphate | 0.04 |
| Sodium salicylate | 0.04 |

TABLE 2-continued

| Ingredients | II-A |
|---|---|
| Glycerin | 0.5 |
| Trideceth-2 carboxamide mea | 1 |
| Cetearyl alcohol (and) ceteareth-25 | 3 |
| Water | QS to 100 |

Example 2

For application, compositions I-A and I-B were respectively mixed with composition II-A at a weight ratio of 1:1, to provide mixtures A-A and B-A. 20 g of the mixtures were each poured in the palm of the hair dressers, who applied the products (mixtures A-A or B-A) immediately onto the middle-length hair, i.e., hair length being about 18 cm and hair weight being 2 g. The hair was massaged around 1 minute and then put onto a hot plate at a constant temperature of 27° C. After 30 minutes, the hair was rinsed with water. The rinsing water was checked and hair color results were observed after blow dry. It was clear to see that, compared with a blank control without adding the retarding combination, the composition I-A resulted in much slower color change during the dyeing, while provided desirable final dyed color. That is, stainless effect was observed for composition I-A during dyeing.

For the stability check of PMP, the colorant samples of I-A and I-B were put into 45° C. oven for 1 month. HPLC was used to analyze the PMP concentration of T0 and after 1 month at 45° C. The results were shown in table 3, demonstrating that I-A did not loss detectable amount (detected as 0.0%) of PMP, significantly better compared with 47.8% loss of I-B.

TABLE 3

| | PMP test result | | | |
|---|---|---|---|---|
| | Theoretical value (%) | T0 (%) | 45° C., 1 M (%) | Loss |
| I-A | 0.50 | 0.48 | 0.48 | 0.0% |
| I-B | 0.50 | 0.46 | 0.24 | −47.8% |

The invention claimed is:

1. A dye kit comprising:
(A) a dyeing composition (A) comprising:
(I) a colorant composition (I), comprising:
i) at least one oxidative dye(s);
wherein the composition (I) is free of ammonia; and
(II) a developer composition (II), comprising:
ii) at least one oxidant; and
(B) a pyrazolone composition (B) comprising
a retarding combination of pyrazolone compound and a reducer, wherein
the pyrazolone compound consists essentially of phenyl methyl pyrazolone, and
the reducer is a thio-organic acid selected from the group consisting of thioglycolic acid, dithio glycolic acid, thiolactic acid, thiomalic acid, and a mixture thereof;
wherein the pyrazolone composition (B)
is placed in a chamber separate from the dyeing composition (A).

2. The dye kit according to claim 1, wherein the developer composition (II) is placed separate from the colorant composition (I).

3. The dye kit according to claim 1, wherein the oxidative dye comprises a dye combination of one or more oxidation bases with one or more couplers;
wherein the oxidation base comprises unsubstituted para-phenylenediamine or a para-phenylenediamine substituted with 1 or 2 C1-C4 alkyl, an unsubstituted para-aminophenol or a para-aminophenol substituted with 1 or 2 C1-C4 alkyl, and 4,5-diaminopyrazoles; and
the coupler comprises unsubstituted meta-aminophenol or a meta-aminophenol substituted with 1 or 2 C1-C4 alkyl, unsubstituted meta-diphenol or a meta-diphenol substituted with 1 or 2 C1-C4 alkyl, diamino-phenols, or unsubstituted hydroxyindoles, an amino substituted hydroxypyridine, or hydroxybenzomorpholine.

4. The dye kit according to claim 1, wherein the colorant composition (I) comprises an antioxidant selected from a natural exogenous phytochemical antioxidant, flavonoid, vitamin C and/or E or a derivative thereof, tocopherols, tocotrienol phenol, carotenoid, anthocyanin, dihydrochalcone, phenylpropanoid, chalcone, curcuminoid, tannin, stilbenoid, coumarin, carotenoid, or a mixture thereof.

5. The dye kit according to claim 4, wherein the antioxidant is used in an amount of from 0.001 to 10% by weight relative to the total weight of the colorant composition (I).

6. The dye kit according to claim 1, wherein the oxidative dye comprises one or more oxidation bases in an amount from 0.0001% to 10% by weight relative to the total weight of the composition (I); and/or the oxidative dye further comprises one or more couplers in an amount from 0.0001% to 10% by weight relative to the total weight of the composition (I).

7. The dye kit according to claim 1, wherein the oxidant is selected from the group consisting of hydrogen peroxide, urea peroxide, alkali metal bromates, peroxy salts; and a polymer complex capable of releasing hydrogen peroxide.

8. The kit according to claim 1, wherein the concentration of the oxidant is from 0.1% by weight to 50% by weight based on the weight of the composition (II).

9. The kit according to claim 1, wherein the reducer is thioglycolic acid.

10. The kit according to claim 1, wherein the pyrazolone compound is present in amounts ranging from 0.01% to 10% by weight relative to the total weight of the composition (I).

11. The kit according to claim 1, wherein for the pyrazolone composition (B), the reducer and the pyrazolone compound are used at a ratio by weight of 1.1:1 to 10:1.

12. The kit according to claim 1, wherein the composition (I) has a pH of 6-11.

13. A process for reducing stain in areas other than the keratin fibers to which a dye composition has been applied, or slowing down reactions of said applied dye or intermediates thereof, comprising
mixing a pyrazolone composition (B) with the dye composition, then applying the dye to keratin fibers, or
applying the pyrazolone composition (B) to a position to which the dye has been applied for less than 10 minutes,
wherein the dye composition comprises
(I) a colorant composition (I) comprising
(i) at least one oxidative dye; and
wherein the composition (I) is free of ammonia; and
(II) a developer composition (II) comprising
at least one oxidant,
wherein the pyrazolone composition (B) comprises a retarding combination of pyrazolone compound and a reducer, in which:

the pyrazolone compound consists essentially of phenyl methyl pyrazolone, and the reducer is a thio-organic acid selected from the group consisting of thioglycolic acid, dithio glycolic acid, thiolactic acid, thiomalic acid, and a mixture thereof.

14. A method for dyeing keratin fibers, while reducing the stain in areas other than the keratin fibers that are contacted by the dyeing composition, comprising applying a dyeing composition (A) to keratin fibers, and applying a pyrazolone composition (B), comprising a retarding combination of a pyrazolone compound and a reducer, to said keratin fibers, in which:

said dyeing composition (A) comprises
(I) a colorant composition (I) comprising
(i) at least one oxidative dye;
wherein the composition (I) is substantially free of ammonia; and
(II) a developer composition (II) comprising
at least one oxidant, wherein
said pyrazolone compound consists essentially of phenyl methyl pyrazolone, and
the reducer is a thio-organic acid selected from the group consisting of thioglycolic acid, dithio glycolic acid, thiolactic acid, thiomalic acid, and a mixture thereof.

* * * * *